Oct. 9, 1962 E. S. BOERNER Plant Pat. 2,181
ROSE PLANT
Filed Oct. 31, 1961
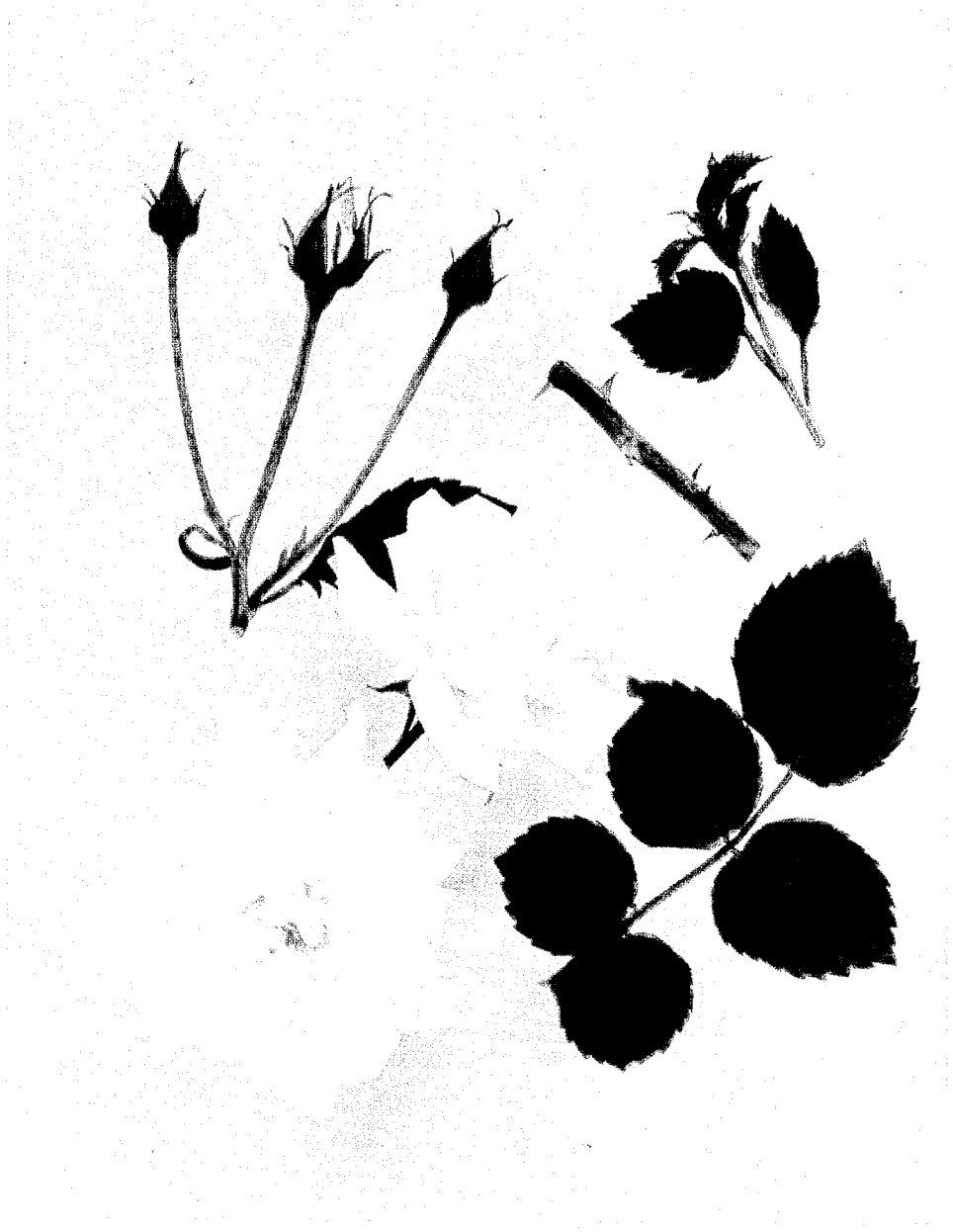
Inventor.
E. S. Boerner
By: Robb & Robb
Attorneys.

United States Patent Office

Plant Pat. 2,181
Patented Oct. 9, 1962

2,181
ROSE PLANT

Eugene S. Boerner, Newark, N.Y., assignor to Jackson & Perkins Company, Newark, N.Y., a corporation of New York Filed Oct. 31, 1961, Ser. No. 149,138
1 Claim. (Cl. 47—61)

The present invention relates to a new and distinct variety of rose plant of the fluoribunda class, which was originated by me by crossing an unnamed and unpatented seedling of "Goldilocks" (Plant Patent No. 672) with an unnamed and unpatented seedling of "Demure" (Plant Patent No. 1,065).

The primary objective of this breeding was to produce a new rose variety in which the firmness of the flower petals that is characteristic of the "Garnette" (unpatented) family is carried over into the new variety, but with the flowers of the new variety being of a different color. The variety "Demure," which is one of the antecedents of my new variety, is a descendant of the rose "Garnette," and as the result of the breeding of my new variety, the aforementioned objectives were fully achieved, along with other desirable improvements, as evidenced by the following unique combination of characteristics which are outstanding in the new variety and which distinguish it from its parents, as well as from all other varieties of which I am aware:

(1) A free blooming habit;
(2) A prolific blooming habit when grown as a greenhouse rose;
(3) Stiff flower petals;
(4) Long-lasting flower qualities; and
(5) A distinctive and attractive general color tonality of the flowers corresponding to Empire Yellow with the upper half of the flower petals lightly overcast with Pinard Yellow.

Asexual reproduction of my new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of my new variety, with color terminology in accordance with Ridgway's Color Standards and Nomenclature:

Parentage: Seedling.
*Seed parent.*—An unnamed seedling of "Goldilocks."
*Pollen parent.*—An unnamed seedling of "Demure."
Classification:
*Botanic.*—Floribunda.
*Commercial.*—Floribunda.

*Flower*

(Observations made from specimens grown in a greenhouse at Newark, New York, in the early morning during the early part of the month of July.)

Blooming Habit: Recurrent—continuous; free.
Bud:
*Size.*—Medium.
*Form.*—Ovoid; is not affected by wet or hot weather.
*Color.*—When sepals first divide—Apricot-Orange, Plate 14. When petals begin to unfurl—Buff-Yellow, Plate 4 with outer edges of petals very lightly overcast with Apricot-Orange, Plate 14. When half-blown: inside of petals—Apricot-Yellow, Plate 4, lightly overcast with Orange-Pink, Plate 2; reverse of petals—Lemon-Chrome, Plate 4, very lightly overcast with Apricot-Yellow, Plate 4.
*Sepals.*—Smooth edge; slightly branched; curl back when petals begin to unfurl. Color: inside—Absinthe-Green, Plate 31; outside—Spinach-Green, Plate 5.
*Calyx.*—Color—Light Bice Green, Plate 17. Shape — funnel. Size — small. Aspect — hairy. Odor when rubbed—none.
*Peduncle.* — Length — medium. Aspect — prickly. Color—Light Bice Green, Plate 17. Strength—erect; slender.
*Opening.*—Opens up well; is not affected by adverse weather conditions.
Bloom:
*Size.* — Medium. Average size when fully expanded—3 inches.
*Borne.*—Both singly and several together; prolific production of flowers in greenhouse.
*Stems.*—Medium length; strong.
*Form (when first open).*—Cupped. Permanence—retains its form to the end, but all petals curl back.
*Petalage.*—Double (full but open center). Number of petals under normal conditions—from 35 to 40.
*Color.*—Center of flower—Lemon-Chrome, Plate 4, lightly overcast with Empire Yellow, Plate 4. Outer petals—Capucine Buff, Plate 3, with upper half of petals lightly overcast with Maize Yellow, Plate 4, and with lower half of petals overcast with Baryta Yellow, Plate 4. Base of petals (aiglet)—Lemon-Chrome, Plate 4. Inside of petals—Empire Yellow, Plate 4, with upper half of petals lightly overcast with Pinard Yellow, Plate 4. Reverse of petals—Pinard Yellow, Plate 4. General tonality from a distance—Empire Yellow, Plate 4, with upper half of petals lightly overcast with Pinard Yellow, Plate 4.
*Discoloration.*—General tonality at end of first day—Empire Yellow, Plate 4, with upper half of petals lightly overcast with Pinard Yellow, Plate 4. Second day—Empire Yellow, Plate 4, with upper half of petals lightly overcast with Pinard Yellow, Plate 4. Third day—Empire Yellow, Plate 4, lightly overcast with Maize Yellow, Plate 4.
Petals:
*Texture.*—Leathery; stiff; is not affected by wet or hot weather.
*Appearance.*—Inside—satiny. Outside—shiny.
*Form.*—Oval.
*Arrangement.*—Imbricated (regularly arranged shingle-like).
*Petaloids in center.*—Few; small.
*Persistence.*—Drop off cleanly.
*Fragrance.*—Moderate. Nature—tea (average hybrid tea scent).
*Lasting quality.*—On the plant—very long. As cut flower—very long (from 8 to 10 days).

*Genital Organs*

Stamens, anthers: Medium size; many; regularly arranged around styles. Color—Orange Buff, Plate 3.
Stamens, filaments (threads): Medium length. Color—Apricot-Yellow, Plate 4.
Pollen: Color—Pale Yellow-Orange, Plate 3.
Styles: Bunched; uneven length; medium length; thin.
Stigmas: Color—Pinard Yellow, Plate 4.
Ovaries: Some protrude from calyx.
Hips: None.
Seeds: None.

*Plant*

Form: Bush.
Growth: Vigorous; upright.
Foliage: Compound of 5–7 leaflets.
*Size.*—Medium.
*Quantity.*—Abundant.
*Color.*—New foliage: upper side—Yellowish Oil Green, Plate 5, lightly overcast with Claret Brown, Plate 1; under side—Brick Red, Plate 13. Old foliage: upper side—Varley's Green, Plate 18; under side—Light Elm Green, Plate 17.
*Shape.*—Oval.
*Texture.*—Upper side—glossy. Under side—smooth.
*Ribs and veins.*—Prominent.
*Edge.*—Serrated (saw-toothed).
*Serration.*—Both double and single; large.
*Leaf stem.*—Color—Brick Red, Plate 13. Under side—prickly.
*Stipules.*—Medium length; slightly bearded.
Wood:
*New wood.*—Color—Parrot Green, Plate 6. Bark—smooth.
*Old wood.*—Color—Spinach Green, Plate 5. Bark—smooth.

Thorns:
*Thorns.*—Quantity: on main stalks from base—ordinary; on laterals from stalk—ordinary. Form—narrow base; medium length; straight. Color (when young)—Eugenia Red, Plate 13. Position—irregular.
*Prickles.*—Quantity: on main stalks—none; on laterals—none.
*Short needles.*—Quantity: on main stalks—none; on laterals—none.

I claim:

A new and distinct variety of rose plant of the floribunda class, substantially as herein shown and described, characterized particularly as to novelty by the unique combination of a free blooming habit, a prolific blooming habit when grown in the greenhouse, stiff flower petals, long lasting flower qualities, and a distinctive and attractive general color tonality of the flowers corresponding to Empire Yellow, with the upper half of the flower petals lightly overcast with Pinard Yellow.

No references cited.